United States Patent
Kasai et al.

(10) Patent No.: US 7,084,181 B2
(45) Date of Patent: Aug. 1, 2006

(54) METHOD FOR DECOMPOSING NONMETALLIC HONEYCOMB PANEL, AND METHOD FOR RECYCLING THE SAME

(75) Inventors: Toru Kasai, Tokyo (JP); Shuntaro Kuriyama, Tokyo (JP); Masatada Yamashita, Kanagawa (JP); Keiichi Miwa, Kanagawa (JP)

(73) Assignees: Jamco Corporation, Tokyo (JP); Ishikawajima-Harima Jukogyo Kabushiki Kaisha, Tokyo (JP)

( * ) Notice: Subject to any disclaimer, the term of this patent is extended or adjusted under 35 U.S.C. 154(b) by 334 days.

(21) Appl. No.: 10/670,289

(22) Filed: Sep. 26, 2003

(65) Prior Publication Data

US 2004/0097776 A1 May 20, 2004

(30) Foreign Application Priority Data

Nov. 14, 2002 (JP) ............................. 2002-330303

(51) Int. Cl.
*C08J 11/04* (2006.01)
*C08F 6/00* (2006.01)

(52) U.S. Cl. .................. 521/45; 528/499; 528/481

(58) Field of Classification Search ............... 528/499, 528/481; 521/45; 588/205
See application file for complete search history.

(56) References Cited

U.S. PATENT DOCUMENTS

| | | | | | |
|---|---|---|---|---|---|
| 4,952,662 | A | * | 8/1990 | Finke et al. | 528/182 |
| 5,149,759 | A | * | 9/1992 | Miess et al. | 528/348 |
| 5,326,791 | A | * | 7/1994 | Saleh et al. | 521/45 |
| 5,840,773 | A | * | 11/1998 | Booij et al. | 521/49 |

* cited by examiner

*Primary Examiner*—N. Bhat
(74) *Attorney, Agent, or Firm*—Westerman, Hattori, Daniels & Adrian, LLP.

(57) ABSTRACT

The present invention treats crushed pieces of a nonmetallic honeycomb panel together with a process water under high-temperature and high-pressure for a predetermined time so as to separate components. Water or alkali-added water is used as process water. The method comprises a first process for treating the crushed pieces for a predetermined time with the water heated and pressurized to a subcritical range to hydrolyze aromatic polyamide, and a second process for treating the same with the water heated and pressurized to a supercritical range, wherein the aromatic polyamide is hydrolyzed and separated in the first process, and dehalogenation is carried out in the second process.

6 Claims, 3 Drawing Sheets

PROCESS OUTLINE

CRITICAL STATUS OF WATER

DECOMPOSITION OF AROMATIC POLYAMIDE m-PHENYLENEDIAMINE          ISOPHTHALIC ACID

METHOD FOR DECOMPOSING NONMETALLIC HONEYCOMB PANEL, AND METHOD FOR RECYCLING THE SAME

FIELD OF THE INVENTION

The present invention relates to a method for decomposing a nonmetallic honeycomb panel, made for example of an aromatic polyamide, used as an interior equipment of an aircraft, and the method for recycling the components of the nonmetallic honeycomb panel.

DESCRIPTION OF THE RELATED ART

Since there are strict fire resistance requirements for the interior equipments used in an aircraft, nonmetallic honeycomb panels made of aromatic polyamide having preferable fire resistance are widely used. However, the discard portion of the panel or the used aromatic polyamide nonmetallic honeycomb panel contains considerable amount of glass fiber, so it was difficult to dispose of by incineration. Therefore, landfill means were relied on as means for disposing such honeycomb panel equipments.

Such honeycomb panels are mainly composed of glass fiber, aromatic polyamide, phenol and fluorine-based film. It is desirable to recycle such components.

SUMMARY OF THE INVENTION

Therefore, the present invention provides a method for recycling the honeycomb panel by decomposing and separating the honeycomb panel into components without using any special solvent or catalyst.

The present invention provides a method for decomposing a nonmetallic honeycomb panel by processing crushed pieces of the nonmetallic honeycomb panel together with a process water under a high temperature and high pressure condition for a predetermined length of time to decompose the nonmetallic honeycomb panel into components.

The method comprises a first step of performing treatment for a predetermined length of time with the process water brought to a subcritical range, the process water being either water or alkali-added water, and a second step of performing treatment for a predetermined length of time with the process water brought to a supercritical range, wherein an aromatic polyamide is hydrolyzed and separated during the first step, and dehalogenation is carried out during the second step.

Further, when the second step is completed, the nonmetallic honeycomb panel is separated into a decomposition product and a glass fiber.

According to the method for recycling a nonmetallic honeycomb panel of the present invention, the method comprises a step of decomposing the nonmetallic honeycomb panel into components by crushing the nonmetallic honeycomb panel and treating the crushed panel together with a process water under a high temperature and high pressure condition for a predetermined length of time; and a step of separating a glass fiber from a decomposition product obtained by the decomposing step, wherein the glass fiber is recycled, and a residue remaining after separating the glass fiber from the decomposition product is used as fuel.

Furthermore, the decomposing step of the recycling method comprises a first step of performing treatment for a predetermined length of time with the process water brought to a subcritical range, and a second step of performing treatment for a predetermined length of time with the process water brought to a supercritical range; wherein an aromatic polyamide is hydrolyzed and separated during the first step, and dehalogenation is carried out during the second step; and when the second step is completed, the nonmetallic honeycomb panel is separated into the decomposition product and the glass fiber.

DETAILED DESCRIPTION OF THE PREFERRED EMBODIMENT

The preferred embodiment of the present invention will now be explained.

In the present embodiment, an example of a nonmetallic honeycomb panel formed of an aromatic polyamide will be illustrated.

Since the nonmetallic honeycomb panel formed of an aromatic polyamide is fire resistant, it is preferably used as a structural member (interior equipment) of an aircraft.

The composition of the nonmetallic (aromatic polyamide) honeycomb panel will be explained in table 1.

TABLE 1

Representative Composition of the Nonmetallic Honeycomb Panel (Weight Ratio)

| Glass Fiber | 40% |
| Phenolic Resin | 35% |
| Aromatic Polyamide | 17% |
| Fluorine-based Film | 8% |

The fluorine-based film prevents contaminants from adhering to the surface of the honeycomb panel. Further, a flame retardant containing halogen such as chlorine or bromine is added to the phenolic resin to assure sufficient fire resistance.

Now, the method for treating the discard portion of the honeycomb panel or the used panel will be explained.

(1) First, the discard portion of the honeycomb panel or the used panel is crushed into small pieces. Then, the crushed honeycomb panel pieces are dipped into water (or alkaline added water).

(2) The water (or alkaline added water) having the honeycomb panel pieces dipped therein is placed inside a hydrothermal reaction apparatus, where it is heated and pressurized. Treatment is carried out for a predetermined length of time, approximately 30 minutes, in a subcritical region with a pressure between 1.5 and 17 MPa and a water temperature between 200 and 350° C. (first treatment).

Figure 1:
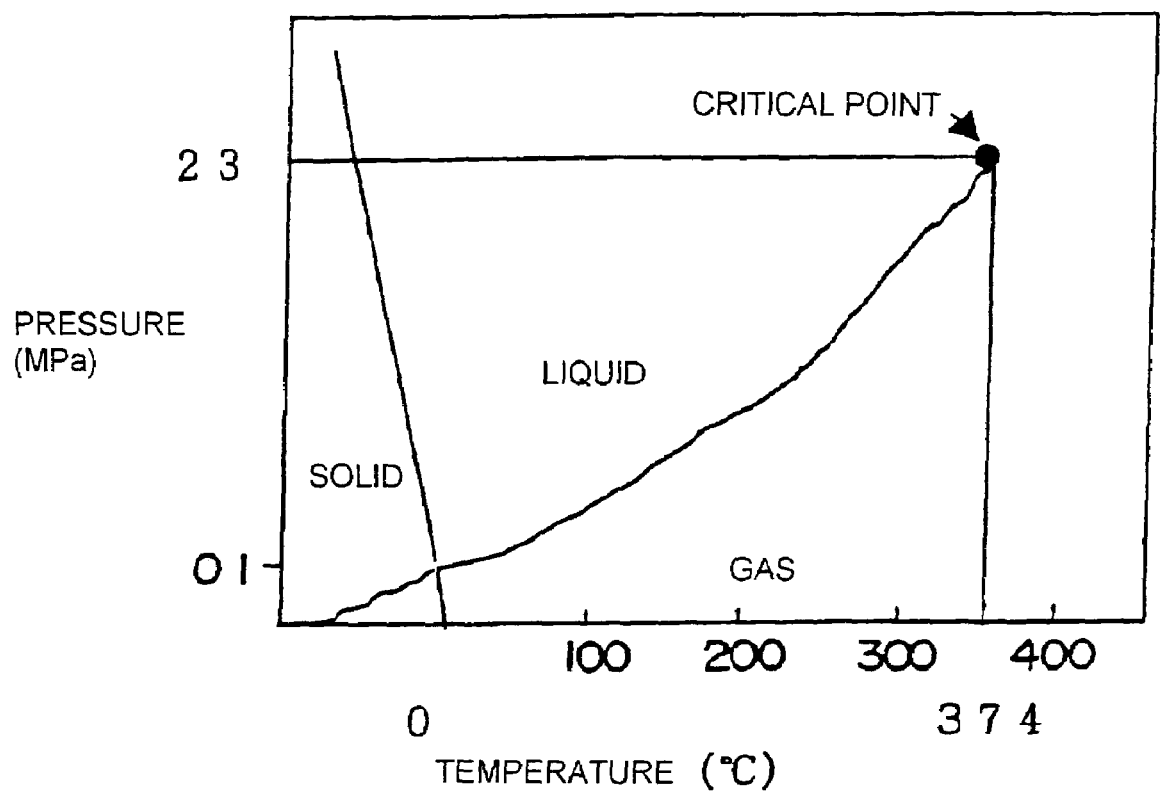
FIG. 1 is a graph showing the change in the critical status of water by pressure and temperature.

When the water is heated and pressurized to reach the critical point (374° C., 23 MPa), the status of the water reaches a critical state between liquid and gas, as shown in FIG. 1. When the temperature and pressure of water exceeds this critical point, the ion product and the dielectric constant of the water changes.

Within the subcritical region (water temperature between 200 and 350° C., pressure between 1.5 and 17 MPa), hydrolysis of the aromatic polyamide of the honeycomb panel pieces occur.

Figure 2:
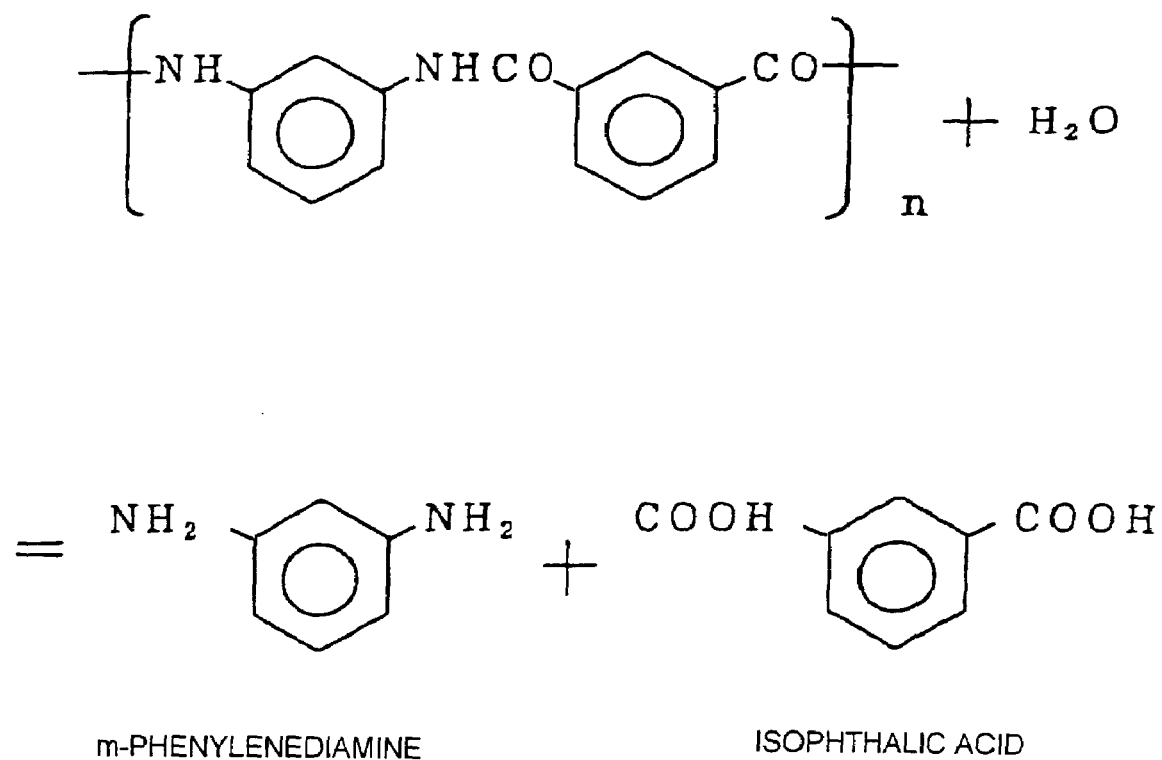
FIG. 2 is an explanatory view of the hydrolysis of aromatic polyamide.

The hydrolysis of the aromatic polyamide in the subcritical region will now be explained with reference to FIG. 2.

As shown, the aromatic polyamide is decomposed into two components, m-phenylenediamine and isophthalic acid, by hydrolysis.

Now, we will explain the relationship between the temperature of the process liquid by which the aromatic polyamide is hydrolyzed and the decomposition recovery percentage.

Experiments were carried out with the process time set to 10 minutes and 30 minutes, and the temperature of the process liquid set to 300° C., 325° C., 350° C. and 375° C., respectively.

The results of the experiments are shown in tables 2 and 3.

TABLE 2

Result of Critical Water Processing (Process Time: 30 min)

| | m-phenylenediamine | Isophthalic acid | Total |
|---|---|---|---|
| Polyamide Paper (325° C.) | 25% | 43% | 68% |
| Polyamide Paper (350° C.) | 30% | 57% | 87% |
| Polyamide Paper (375° C.) | 25% | 51% | 76% |

(% by weight)

TABLE 3

Recovery Percentage according to Condition (% by Weight)

| | m-phenylenediamine | | | Isophthalic acid | | | Total | | |
|---|---|---|---|---|---|---|---|---|---|
| | 10 min | 30 min | 10 min NaOH | 10 min | 30 min | 10 min NaOH | 10 min | 30 min | 10 min NaOH |
| 300° C. | 0% | | 19% | 2% | | 44% | 2% | | 63% |
| 325° C. | 1% | 13% | 18% | 6% | 24% | 50% | 8% | 37% | 68% |
| 350° C. | 5% | 22% | 20% | 13% | 43% | 54% | 18% | 65% | 74% |
| 375° C. | 13% | 20% | 21% | 21% | 40% | 54% | 35% | 60% | 75% |

As shown in the experiment results, the decomposition recovery percentage of the two components, m-phenylenediamine and isophthalic acid, were highest when the temperature of the process liquid was 350° C.

(3) The process liquid is heated and pressurized to a supercritical region (374° C. or higher, 23 MPa or higher) (second treatment).

After separating the aromatic polyamide into m-phenylenediamine and isophthalic acid by hydrolysis, the residue is processed at 375° C. and 23 MPa (supercritical point of water) for 30 minutes. The decomposition reaction of the residue that remains after isolating m-phenylenediamine and isophthalic acid is accelerated under the supercritical status.

By this process, phenolic resin and fluorine-based film are hydrolyzed.

The halogen-based substance created during reaction is neutralized (dehalogenated) with a neutralizer.

(4) Finally, the remaining low-molecularized phenols and glass fiber are separated. The thus decomposed, separated and recovered phenols are reused as fuel. Further, glass fiber is recycled as filler or raw material.

Figure 3:
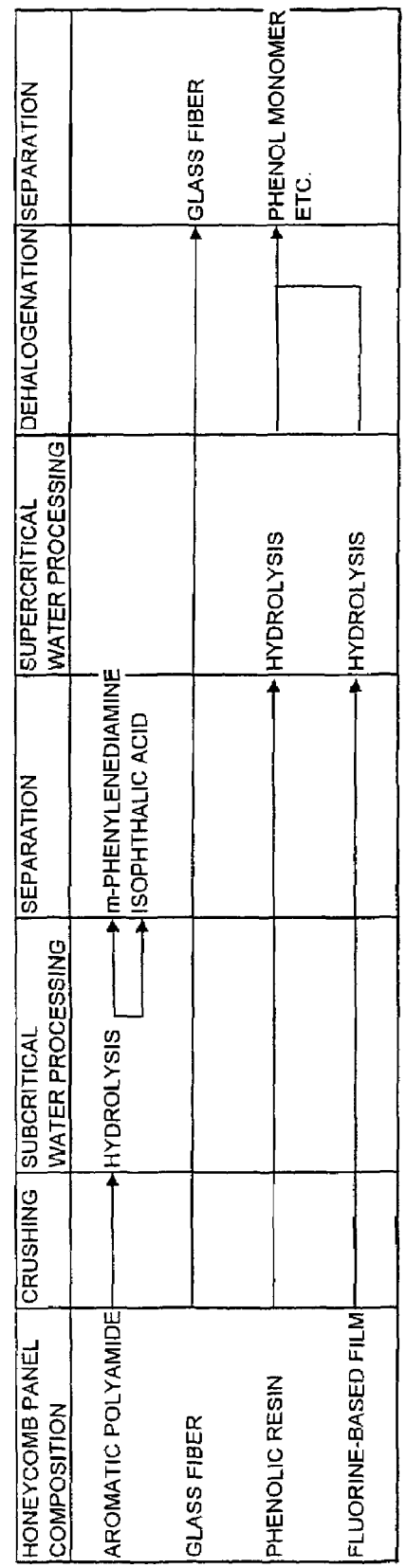
FIG. 3 is an explanatory view showing the outline of the process for decomposing and separating the nonmetallic honeycomb panel.

The decomposition and separation process of each material constituting the nonmetallic honeycomb panel is shown in FIG. 3.

The aromatic polyamide is hydrolyzed by subcritical water processing and separated into m-phenylenediamine and isophthalic acid.

Glass fiber is separated from the final residue.

The phenolic resin and the fluorine-based film are hydrolyzed by supercritical water processing and separated as phenol monomer from the final residue.

The finally separated glass fiber is recycled and the phenol monomer is reused as fuel.

According to the present invention, a nonmetallic honeycomb panel can be recycled by decomposing and separating the components of the panel without using any special solvent or catalyst.

What is claimed is:

1. A method for decomposing a nonmetallic honeycomb panel by processing crushed pieces of the nonmetallic honeycomb panel together with a process water under a high temperature and high pressure condition for a predetermined length of time to decompose said nonmetallic honeycomb panel into components, wherein the nonmetallic honeycomb panel comprises aromatic polyamide and halogen components, said method comprising:

a first step of performing treatment for a predetermined length of time with said process water brought to a subcritical range, said process water being either water or alkali-added water; and a second step of performing treatment for a predetermined length of time with said process water brought to a supercritical range;

wherein an aromatic polyamide is hydrolyzed and separated during said first step, and dehalogenation is carried out during said second step.

2. The method for decomposing a nonmetallic honeycomb panel according to claim 1, wherein when said second step is completed, said nonmetallic honeycomb panel is separated into a decomposition product and a glass fiber.

3. A method for recycling a nonmetallic honeycomb panel, wherein the nonmetallic honeycomb panel comprises aromatic polyamide and halogen components, said method comprising:

a step of decomposing said nonmetallic honeycomb panel into components by crushing said nonmetallic honeycomb panel and treating said crushed panel together with a process water under a high temperature and high pressure condition for a predetermined length of time; and a step of separating a glass fiber from a decomposition product obtained by said decomposing step, wherein said glass fiber is recycled, and a residue remaining after separating said glass fiber from said decomposition product is used as fuel.

4. The method for recycling a nonmetallic honeycomb panel according to claim 3, wherein said decomposing step comprises a first step of performing treatment for a predetermined length of time with said process water brought to a subcritical range, and a second step of performing treatment for a predetermined length of time with said process water brought to a supercritical range;

wherein an aromatic polyamide is hydrolyzed and separated during said first step, and dehalogenation is carried out during said second step; and when said second step is completed, said nonmetallic honeycomb panel is separated into said decomposition product and said glass fiber.

5. The method for decomposing a nonmetallic honeycomb panel according to claim 1, wherein said first step is performed for a predetermined length of time of about 30 minutes and said process water is brought to a subcritical range of about 200 to 350° C. and 1.5 to 17 MPa, and said second step is performed for a predetermined length of time of about 30 minutes.

6. The method for recycling a nonmetallic honeycomb panel according to claim 4, wherein said first step is performed for a predetermined length of time of about 30 minutes and said process water is brought to a subcritical range of about 200 to 350° C. and 1.5 to 17 MPa, and said second step is performed for a predetermined length of time of about 30 minutes.

* * * * *